(12) United States Patent
Eldredge

(10) Patent No.: US 8,388,600 B1
(45) Date of Patent: Mar. 5, 2013

(54) APPARATUS, SYSTEM, AND METHOD FOR TREATING ATYPICAL HEADACHES

(71) Applicant: Stephen Eldredge, South Jordan, UT (US)

(72) Inventor: Stephen Eldredge, South Jordan, UT (US)

(73) Assignee: Dolor Technologies, Salt Lake City, UT (US)

( * ) Notice: Subject to any disclaimer, the term of this patent is extended or adjusted under 35 U.S.C. 154(b) by 0 days.

(21) Appl. No.: 13/629,997

(22) Filed: Sep. 28, 2012

(51) Int. Cl.
*A61M 31/00* (2006.01)
(52) U.S. Cl. ....................... 604/514
(58) Field of Classification Search ............. 604/514, 604/528
See application file for complete search history.

(56) References Cited

U.S. PATENT DOCUMENTS

| | | | |
|---|---|---|---|
| 4,886,493 A * | 12/1989 | Yee | 604/516 |
| 6,350,465 B1 * | 2/2002 | Jonnalagadda et al. | 424/434 |
| 6,413,499 B1 * | 7/2002 | Clay | 424/49 |
| 6,491,940 B1 * | 12/2002 | Levin | 424/434 |
| 6,853,858 B2 * | 2/2005 | Shalev | 607/3 |
| 7,877,147 B2 * | 1/2011 | Shalev et al. | 607/45 |
| 8,231,588 B2 * | 7/2012 | Xia | 604/275 |
| 2001/0004644 A1 * | 6/2001 | Levin | 514/646 |
| 2010/0030188 A1 * | 2/2010 | Xia | 604/514 |

* cited by examiner

*Primary Examiner* — Nicholas Lucchesi
*Assistant Examiner* — Jenna Zhang
(74) *Attorney, Agent, or Firm* — Baker Hostetler, LLP

(57) ABSTRACT

An apparatus, system, and method are disclosed for facilitating intranasal administration of a medication to a patient's sphenopalatine/pterygopalatine recess. The apparatus includes a catheter having a lumen disposed therethrough, the catheter comprising an insertion end and a manipulation end, the insertion end having an intrinsic curvature with respect to a longitudinal axis of the catheter such that the insertion end of the catheter lies in a first plane and the manipulation end lies in a second plane, wherein the catheter smoothly transitions between the first plane and the second plane, the intrinsic curvature conforming to a patients nasal anatomy such that the catheter may be inserted into a sphenopalatine/pterygopalatine recess. The apparatus also includes a straightening member configured to removably engage the catheter. The straightening member straightens the intrinsic curvature such that the first plane and the second plane are aligned when the catheter is engaged by the straightening member.

10 Claims, 11 Drawing Sheets

APPARATUS, SYSTEM, AND METHOD FOR TREATING ATYPICAL HEADACHES

CROSS-REFERENCE TO RELATED APPLICATION

This application is a divisional of U.S. patent application Ser. No. 12/553,953 filed on Sep. 3, 2009, which claims the benefit of U.S. Provisional Application 61/094,323 filed on Sep. 4, 2008. The entire disclosures of application Ser. Nos. 12/553,953 and 61/094,323 are incorporated herein by reference, as if fully set forth herein.

FIELD OF ART

This invention relates to parasympathetic nerve blockade and more particularly relates to blockade of sphenopalatine/pterygopalatine ganglia.

BACKGROUND OF THE ART

Sympathetic pain is a type of nerve pain that arises due to abnormalities in the function of the sympathetic nervous system. With sympathetic pain an abnormality in a group of nerves called a ganglion cause pain to an organ or body region. To treat sympathetic pain physicians can block a ganglion with the injection of medication into a specific area of the body. To therapeutically treat acute pain a physician injects a local anesthetic into the affected neuronal ganglion. This type of treatment may be referred to as a nerve block.

The sphenopalatine/pterygopalatine ganglia is a neuronal structure located principally in the center of the head in the pterygopalatine fossa posterior to the middle turbinate. The sphenopalatine/pterygopalatine ganglia comprises the largest cluster of sympathetic neurons in the head outside of the brain. The sphenopalatine/pterygopalatine ganglia interfaces and directs nerve impulses to the majority of the head's autonomic or parasympathetic pathways. Therefore, any abnormality or injury to this structure may cause severe pain. A nerve block of the sphenopalatine/pterygopalatine ganglia is effective in relief in a variety of pain conditions ranging from headache to lower back pain. Additionally, other disease processes such as headache disorders and other neurological conditions can be arrested, or improved by local anesthetic blockade, and/or other pharmacological augmentation or mechanical alteration of the sphenopalatine/pterygopalatine ganglia and surrounding structures.

Unfortunately, because of the anatomical position of the sphenopalatine/pterygopalatine ganglia, the structure is very difficult to block with a local anesthetic solution. The anatomical location of the sphenopalatine/pterygopalatine ganglia is dangerously close to many vital and delicate mid brain structures. Although direct needle placement can be employed under fluoroscopic guidance to administer anesthetic to the sphenopalatine/pterygopalatine ganglia, most practitioners will not attempt the procedure due to the technical difficulty and extreme dangers of an aberrant needle placement.

SUMMARY

From the foregoing discussion, it should be apparent that a need exists for an apparatus, system, and method for treating parasympathetic nerve pain in the sphenopalatine/pterygopalatine ganglia. Beneficially, such an apparatus, system, and method would administer medication directly to the sphenopalatine/pterygopalatine ganglia.

The present invention has been developed in response to the present state of the art, and in particular, in response to the problems and needs in the art that have not yet been fully solved by currently available local anesthetic blockade methods, systems and apparatus for administering medication to a patient's sphenopalatine/pterygopalatine ganglia. Accordingly, the present invention has been developed to provide an apparatus, system, and method for performing a nerve block of the sphenopalatine/pterygopalatine ganglia that overcome many or all of the above-discussed shortcomings in the art.

The apparatus, in one embodiment, includes a catheter, a straightening member, a spray orifice and a medication delivery port. In certain embodiments the catheter has a lumen disposed therethrough. The catheter includes an insertion end and a manipulation end. The insertion end of the catheter has an intrinsic curvature with respect to a longitudinal axis of the catheter such that the insertion end of the catheter lies in a first plane and the manipulation end lies in a second plane. The catheter smoothly transitions between the first plane and the second plane such that the intrinsic curvature is rounded and conforms to a patient's nasal anatomy. In certain embodiments the intrinsic curvature allows the catheter to be inserted into a sphenopalatine/pterygopalatine recess with minimum discomfort to the patient.

In one embodiment the straightening member is configured to removably engage the catheter. The straightening member straightens the intrinsic curvature of the insertion end such that the first plane and the second plane are aligned when the catheter is engaged by the straightening member. Thus, with the intrinsic curvature of the catheter straightened, the catheter can easily be inserted into a patients nasal cavity.

The spray orifice is located adjacent to the insertion end of the catheter. The spray orifice is in fluid communication with the lumen which is in communication with the medication delivery port. The medication delivery port is located adjacent to the manipulation end of the catheter and is configured to receive a medication and deliver the medication through the lumen to the spray orifice.

The apparatus, in one embodiment, also includes a second lumen. The straightening member in certain embodiments includes a stylus configured to be received within the second lumen. In one embodiment the stylus is keyed to fit within the second lumen in one predefined orientation. In such an embodiment the stylus may identity a direction of the intrinsic curvature when the stylus is disposed within the second lumen. The stylus may also include a finger tab for manipulating the catheter.

In another embodiment the straightening member may be a sleeve configured to receive the catheter. In such an embodiment the sleeve may be configured to straighten the intrinsic curvature of the catheter when the catheter is received within the sleeve.

In one embodiment the apparatus may also include a rotational direction indicator that identifies a direction of the intrinsic curvature when the catheter is placed within the patient's nasal cavity. Thus, a physician may be able to identify the rotational direction of the spray orifice without being able to see the spray orifice or intrinsic curvature. Similarly, in certain embodiments the apparatus may include a depth indicator located on the catheter to identifying a defined depth. In one embodiment the defined depth is a depth equaling a distance between an entrance to a patient's sphenopalatine/pterygopalatine recess and an external entrance to the patient's nostril. In certain embodiments the apparatus includes a second depth indicator located on the catheter. The second depth indicator may identify a second defined depth. The second defined depth may be a depth equaling a distance between a location at a posterior position within a patient's sphenopalatine/pterygopalatine recess and an external entrance to the patient's nostril. In one embodiment the depth indicators are moveable on the catheter so that a physician can adjust a position of the depth indicator according to a patient's nasal anatomy. In another embodiment the depth indicators may be preposition to identify the typical distance between a patient's external opening of a nostril and the patient's sphenopalatine/pterygopalatine recess. The typical distance between a patient's external opening of a nostril and the patient's sphenopalatine/pterygopalatine recess may vary according to a patient's gender or age.

A method of the present invention is also presented for treating migraines. The method in the disclosed embodiments substantially includes the steps necessary to carry out the functions presented above with respect to the operation of the described apparatus. In one embodiment, the method includes inserting a catheter and a straightening member into a nostril of a patient, advancing the catheter and the straightening member past a middle sinus turbinate in the nostril of the patient. The catheter includes an insertion end and a manipulation end. The insertion end has an intrinsic curvature with respect to a longitudinal axis of the catheter such that the insertion end of the catheter lies in a first plane and the manipulation end lies in a second plane. The catheter smoothly transitions between the first plane and the second plane with the intrinsic curvature conforming to a patient's nasal anatomy. This allows the catheter to easily be inserted into a sphenopalatine/pterygopalatine recess. The straightening member removably engages the catheter and straightens the intrinsic curvature of the insertion end such that the first plane and the second plane are aligned when the catheter is engaged by the straightening member.

The method also may include removing the straightening member from the catheter such that the catheter bends in a direction towards a sphenopalatine/pterygopalatine recess of the patient and advancing the catheter into the sphenopalatine/pterygopalatine recess. In certain embodiments the method also includes dispensing a medication to a sphenopalatine/pterygopalatine ganglia disposed within the sphenopalatine/pterygopalatine recess of the patient.

In a further embodiment, the method includes identifying a direction of the intrinsic curvature and aligning the intrinsic curvature of the catheter with the patient's sphenopalatine/ptervgopalatine recess. In another embodiment the method includes identifying a defined depth of the catheter. In one embodiment the defined depth is a depth equaling a distance between an entrance to a patient's sphenopalatine/pterygopalatine recess and an external entrance to the patient's nostril.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
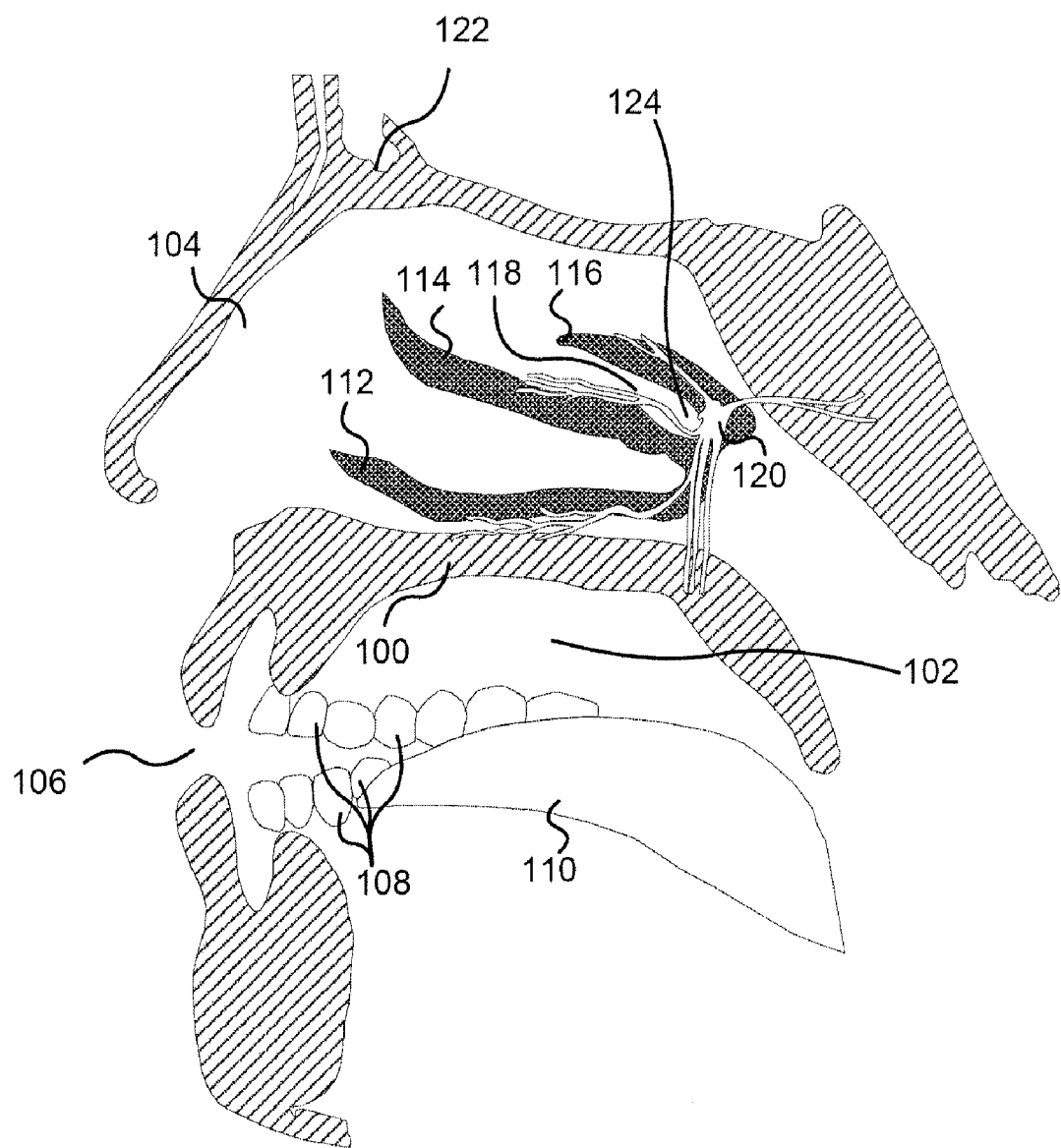
FIG. 1 is a cutaway view illustrating one embodiment of the facial anatomy of a patient upon which the apparatus, system and method of the present invention may be employed.

FIG. 1 is an illustration of the environment in which the present invention may be practiced. In particular, FIG. 1 depicts a cutaway view of the anatomical features of a typical human nasal cavity. One skilled in the art will recognize that certain anatomical features and structures of the human nasal cavity have been omitted to avoid obscuring the structures relevant to the practice of the current invention. To help orient the reader, the mouth 106 is illustrated with teeth 108 and tongue 110. The anatomical structures relevant to the practice of the current invention include the palate 100 which separates the oral cavity 102 from the nasal cavity 104, the inferior sinus turbinate 112, the middle sinus turbinate 114 and tlhe superior sinus turbinate 116 as well as the nasal bone 122. The middle sinus turbinate 114 and superior sinus turbinate 116 define the sphenopalatine/pterygopalatine recess 118. Deep within the sphenopalatine/pterygopalatine recess 118 at the posterior 124 of the sphenopalatine/pterygopalatine recess 118 lies the sphenopalatine/pterygopalatine ganglia 120.

One skilled in the art will recognize that the medical community is not uniform in the terminology with regard to the sphenopalatine or pterygopalatine ganglia. Certain practitioners use sphenopalatine while others use pterygopalatine. Therefore, the present description will refer to the ganglia labeled 120 as the sphenopalatine/pterygopalatine ganglia 120. Similarly, the recess labeled 118 will be referred to as the sphenopalatine/pterygopalatine recess 118. However, this terminology is in no way limiting on the structure for which the present invention is intended. Where practitioners or scientist differentiate between the sphenopalatine ganglia or the pterygopalatine ganglia, the present disclosure will be understood to apply to either structure.

Sympathetic pain is a type of nerve pain that arises due to abnormalities in the function of the sympathetic nervous system. The majority of the "treatment resistant" headache population in the world suffers from what is now properly identified as "Sympathetic Mediated Cephalgia" a particular type of sympathetic pain. With sympathetic pain an abnormality in a group of nerves called a ganglion cause pain to an organ or body region. To treat sympathetic pain physicians can block a ganglion with the injection of medication into a specific area of the body. To therapeutically treat acute pain a physician injects a local anesthetic into the affected neuronal ganglion. This type of treatment may be referred to as a nerve block.

The sphenopalatine/pterygopalatine ganglia 120 is a neuronal structure located principally in the center of the head in the pterygopalatine fossa posterior to the middle turbinate 114. The sphenopalatine/pterygopalatine ganglia 120 comprises the largest cluster of sympathetic neurons in the head outside of the brain. The sphenopalatine/pterygopalatine ganglia 120 interfaces and directs nerve impulses to the majority of the head's autonomic or parasympathetic pathways. Therefore, any abnormality or injury to this structure may cause severe pain. A nerve block of the sphenopalatine/pterygopalatine ganglia 120 is effective in relief in a variety of pain conditions ranging from headache to lower back pain. Additionally, other disease processes such as headache disorders and other neurological conditions can be arrested, or improved by local anesthetic blockade, and/or other pharmacological augmentation or mechanical alteration of the sphenopalatine/pterygopalatine ganglia 120 and surrounding structures.

Unfortunately, because of the anatomical position of the sphenopalatine/pterygopalatine ganglia 120, the structure is very difficult to block with a local anesthetic solution. The anatomical location of the sphenopalatine/ptervgopalatine ganglia 120 is dangerously close to many vital and delicate mid brain structures. Although direct needle placement can be employed under fluoroscopic guidance to administer anesthetic to the sphenopalatine/pterygopalatine ganglia 120, most practitioners will not attempt the procedure due to the technical difficulty and extreme dangers of an aberrant needle placement.

Figure 2:
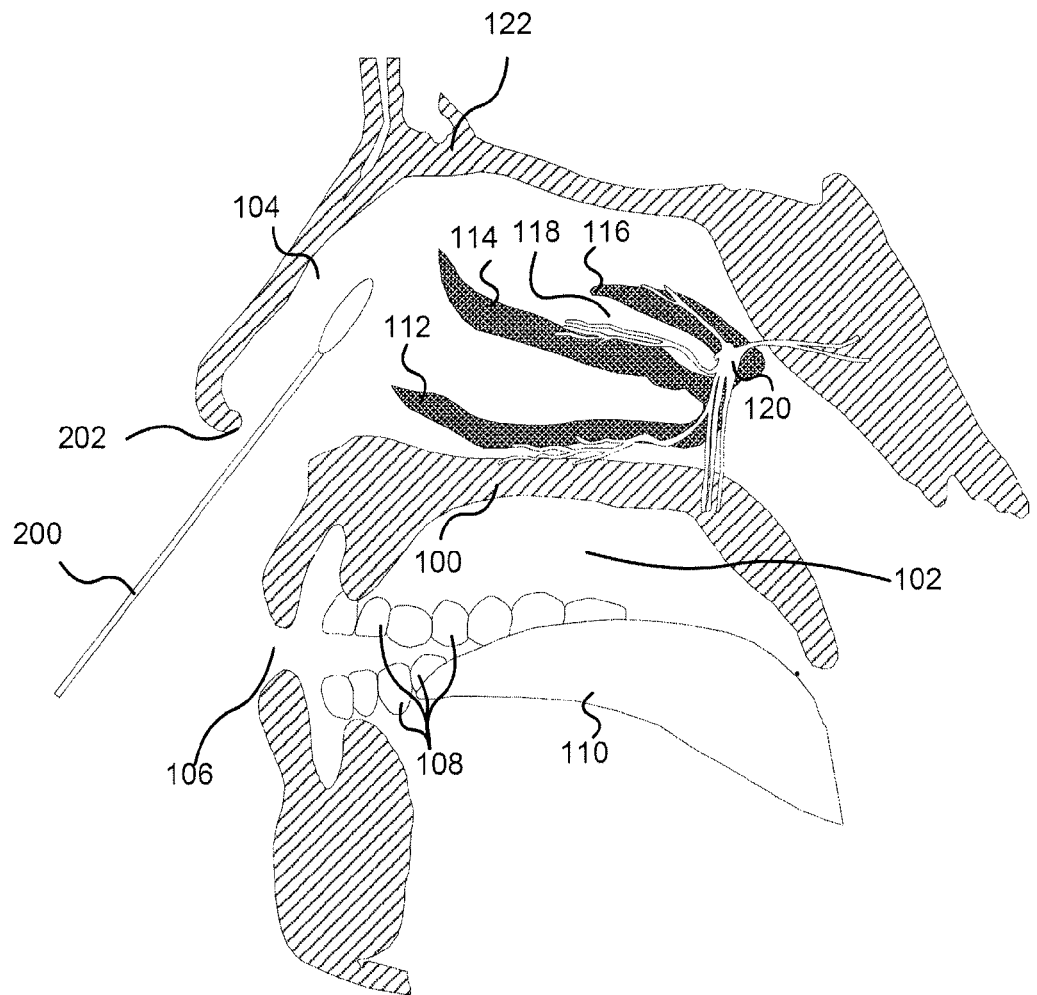
FIG. 2 is a cutaway view illustrating a prior art method of treating headaches.

As shown in the prior art illustration depicted in FIG. 2, the sphenopalatine/pterygopalatine ganglia 120 lies deep within the sphenopalatine/pterygopalatine recess 118. Conventional methods undertaken by pain specialists, neurologists, and neurosurgeons, include the use of an eight inch cotton-tipped applicator 200 saturated with a local anesthetic. Because a cotton-tipped applicator 200 is used, the procedure is referred to as the "Q-tip" procedure. The cotton-tipped applicator 200 is soaked in a vial of concentrated local anesthetic solution. In certain embodiments the anesthetic solution is lidocaine, cocaine, etidocaine or prilocalne, or other non-specified local anesthetic agents. The cotton-tipped applicator 200 is then advanced into the nostril 202 and through the nasal cavity 104. To reach the sphenopalatine/pterygopalatine ganglia 120 in the sphenopalatine/pterygopalatine recess 118, the cotton-tipped applicator 200 must be advanced into the nasal cavity 104 past the middle sinus turbinate 114 and into the sphenopalatine/pterygopalatine recess 118.

Figure 3:
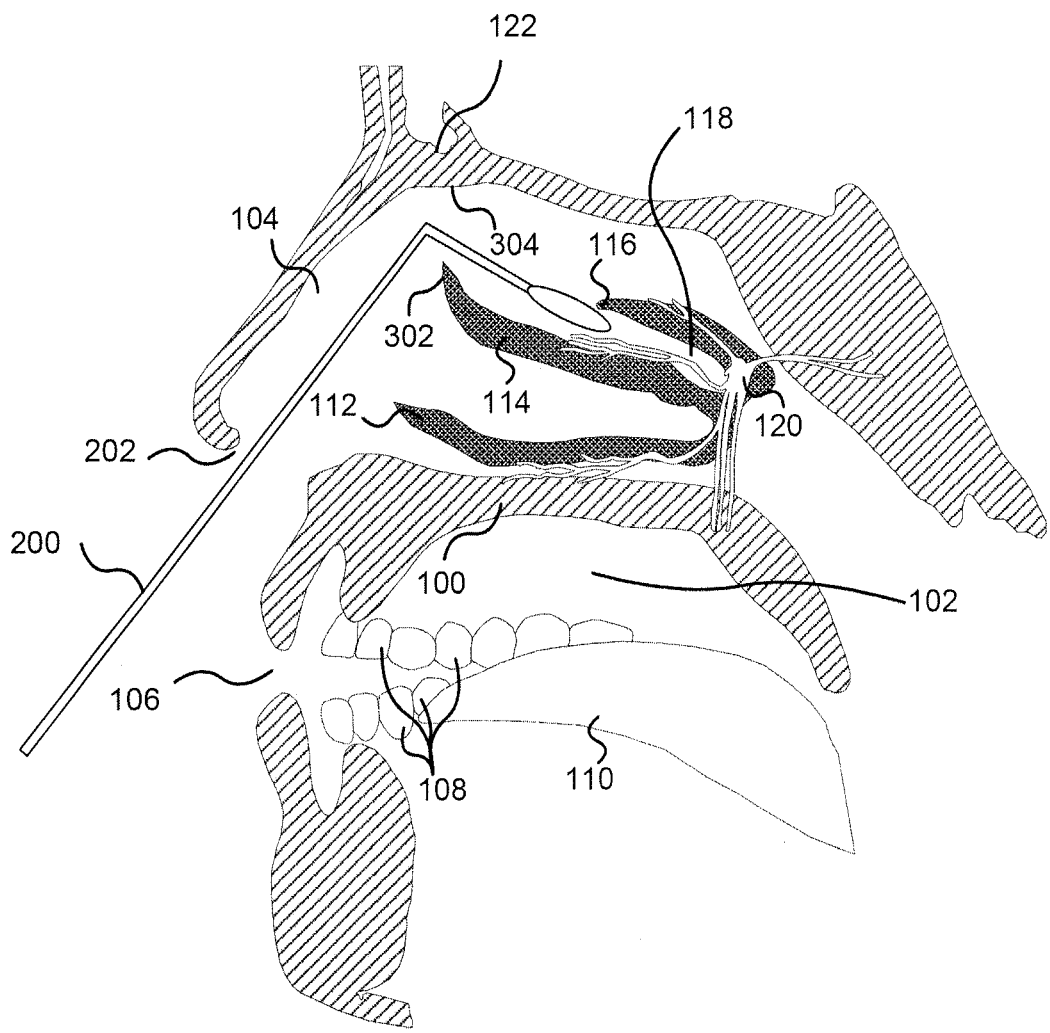
FIG. 3 is a cutaway view illustrating a prior art method of treating headaches.

FIG. 3 illustrates the tortuous path the cotton-tipped applicator 200 of the prior art must traverse to reach the sphenopalatine/pterygopalatine recess 118. To perform the procedure the patient is placed in a supine position. The cotton-tipped applicator 200 is soaked in a vial of concentrated local anesthetic solution. The physician then inserts the cotton-tipped applicator 200 into the patients nostril 202 and through the nasal cavity 104. Advancing the straight, rigid cotton-tipped applicator 200 into the sphenopalatine/pterygopalatine recess 118 can be difficult and painful for the patient as the cotton-tipped applicator 200 must be inserted almost parallel to the patient's face to clear the anterior ridge 302 of the middle sinus turbinate 114. The cotton-tipped applicator 200 must then make an almost 90° bend to avoid the inferior surface 304 of the nasal bone 122 and access the sphenopalatine/pterygopalatine recess 118. The cotton-tipped applicator 200 is left in the patient's sphenopalatine/ptervgopaiatine recess 118 for approximately minutes to allow diffusion of the local anesthetic through the sinus mucosa to depolarize the sphenopalatine/pterygopalatine ganglia 120 to block nerve transmission.

The use of a straight and rigid cotton-tipped applicator 200 that must make some fairly tortuous directional changes around some very sensitive, richly vascular, friable, highly innervated structures complicates the procedure to the point that many practitioners will not attempt it. Known complications include extreme patient discomfort, nosebleeds and the complications associated with nosebleeds including venous-irritating nuisances, arterial hemorrhaging, aspiration, hematochezia or even death. Other complications include local anesthetic toxicity, seizure, iatrogenic foreign bodies such as a broken cotton-tipped applicator 200, sinus mucosal tears and infection.

Anesthetic blockade of any neuronal structure requires direct physical interaction between the anesthetic solution and the targeted tissue. Therefore, to work, the cotton-tipped applicator 200 must deliver the anesthetic solution directly to the sphenopalatine/pterygopalatine ganglion 120. The correct placement of the cotton-tipped applicator 200 is technically challenging and many practitioners simply miss the desired structure, the sphenopalatine/pterygopalatine ganglion 120 when attempting to perform the procedure. To help make the complicated bend required to reach the sphenopalatine/pterygopalatine recess 118 many practitioners will soak the top 2 inches of the cotton-tipped applicator 200 and manipulate the stem to render it flexible so that the patient is less agitated and bleeding risks are lessened. Even with a flexible cotton-tipped applicator 200 the procedure is difficult. Common failure placements include the inferior surface 304 of the nasal bone 122 and the anterior ridge 302 of the middle sinus turbinate 114. When the cotton-tipped applicator 200 is misplaced, a "wring-out" effect may occur wherein the anesthetic is wrung out of the cotton-tipped applicator before it is delivered to the sphenopalatine/pterygopalatine ganglion 120 resulting in an ineffective procedure. Further, as discussed above, the rich vascular and neuronal structure of the nasal cavity 104 makes any misplacement of the cotton-tipped applicator 200 both dangerous and painful.

Figure 4:
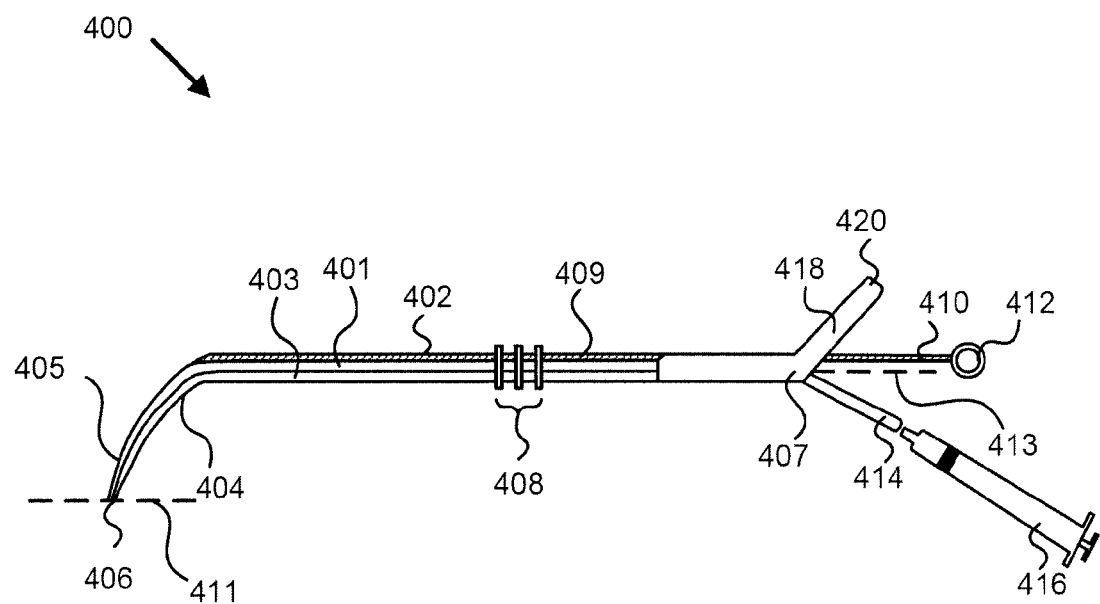
FIG. 4 is a side view illustrating one embodiment of a sphenocath apparatus for treating headaches in accordance with the present invention.

FIG. 4 illustrates a sphenocath 400 including a catheter 402 having an insertion end 405 and a manipulation end 407. In certain embodiments the catheter 402 includes multiple lumens 401 and 403. The catheter 402 has an intrinsic curvature 404, a spray orifice 406, depth indicators 408, a straightening member 409 such as stylus 410 with a pull tab 412, a medication delivery port 414, a syringe 416, a rotational direction indicator 418 and a rotation tab 420.

In certain embodiments the sphenocath 400 comprises a soft sialastic double lumen catheter 402 which is about 24 cm long. One of skill in the art will recognize that the length of the catheter 402 may be varied according to the anatomy of the patient. One of the lumens 401 or 403 is configured to deliver an anesthetic or medication to the sphenopalatine/pterygopalatine recess 118. In certain embodiments the other lumen 401 or 403 is closed distally approximately 1.5 cm from spay orifice 406. For example, in certain embodiments lumen 401 comprises a housing for stylus 410 and is closed at its distal end near the spray orifice 406. The stylus 410 is slideably received within the lumen 401 and may be removed from within the lumen 401 by pulling on the pull tab 410.

As discussed in further detail below with reference to FIGS. 7 and 8, the sphenocath 400 is inserted into the nasal cavity 104 of a patient lying in a supine position. Depth indicators 408 identify when the sphenocath 400 has been inserted into a patients nasal cavity 104 at a depth sufficient to pass the middle sinus turbinate 114. In certain embodiments additional depth indicators (not shown) may indicate a depth sufficient to identify when the tip of the sphenocath 400 is within the sphenopalatine/pterygopalatine recess 118. One skilled in the art will appreciate that depth indicators 408 may vary depending on anatomical variables of the patient such as age and/or gender. The depth indicators 408 may comprise a visual cue such as a line or other such indicator or the depth indicators 408 may comprise a physical structure configured to arrest further insertion of the sphenocath 400. In certain embodiments the sphenocath 400 may be individually sized to fit only one size of a patient. Thus, the sphenocath 400, in certain embodiments, may comprise a large, medium or small size to be used with patients with large, medium or small anatomies. In another embodiment the depth indicators 408 are adjustable such that the depth indicators 408 can be slid along the sphenocath 400 to a position which indicates a depth sufficient to identify when the tip of the sphenocath 400 is within the sphenopalatine/pterygopalatine recess 118 of a particular patient.

The intrinsic curvature 404 of the catheter 402 causes the catheter 402 to bend such that the insertion end 405 of the catheter 402 lies in a first plane as indicated by line 411 while the manipulation end 407 of the catheter 402 lies in a second plane as indicated by line 413. The catheter 402 smoothly transitions between the first plane 411 and the second plane 413 such that the intrinsic curvature 404 conforms to a patient's nasal anatomy. The intrinsic curvature 404 allows the catheter 402 to be inserted into a patient's sphenopalatine/pterygopalatine recess 118 to direct a medication to the patient's sphenopalatine/pterygopalatine ganglia 120.

Rotational direction indicator 418 identifies the rotational configuration of the sphenocath 400. Because the end of the sphenocath 400 has an intrinsic curvature 404, it is beneficial for the physician to know which direction the curvature is pointing to manipulate the sphenocath 400 into the sphenopalatine/pterygopalatine recess 118. In certain embodiments the rotational direction indicator 418 is configured to signal the physician that the intrinsic curvature 404 and thus the spray orifice 406 is pointing in a downward angle when the rotational direction indicator 418 is pointing up. While the embodiment illustrated in FIG. 4 shows the rotational direction indicator 418 as a separate structure, one skilled in the art will recognize that the rotational direction may simply be a line on top of the sphenocath indicating which direction the spray orifice 406 is pointing. In one embodiment, such as the embodiment shown in FIG. 4, the rotational direction indicator 418 may also comprise a rotation tab 420 to assist the physician in manipulating the sphenocath 400 into the sphenopalatine/pterygopalatine recess 118 by providing the physician a leverage point to rotate the sphenocath 400 and align the spray orifice with the sphenopalatine/pterygopalatine recess 118 or sphenopalatine/ptervgopalatine ganglia 120.

Once the sphenocath 400 is manipulated into the sphenopalatine/pterygopalatine recess 118 the syringe 416 injects an antithetic or medication into the medication delivery port 414 and through one of the lumens 401 or 403. The spray orifice 406 is in fluid communication with the lumen (401 or 403) that receives the medication, thus, as the physician injects or dispenses the medication into medication delivery port, the medication travels through the lumen (401 or 403), through the spray orifice 406, and into the sphenopalatine/pterygopalatine recess 118. One skilled in the art will recognize that any metered medicinal or anesthetic delivery means may be substituted for the syringe 416 without departing from the scope of the present invention.

The spray orifice 406 may be configured to deliver a stream of medication or anesthetic. In one embodiment the spray orifice 406 may be configured to disperse the medication or anesthetic such that the area surrounding the sphenopalatine/pterygopalatine ganglia 120 is completely saturated with anesthetic or medication. In certain embodiments the spray orifice 406 may be configured to administer the medication or anesthetic in a controlled fine mist. Further, one of skill in the art will recognize that in certain embodiments the spray orifice 606 may be adjustable such that the physician may dispense the medication in a broader or narrower pattern as dictated by the procedure and the patient's nasal anatomy.

Figure 5A:
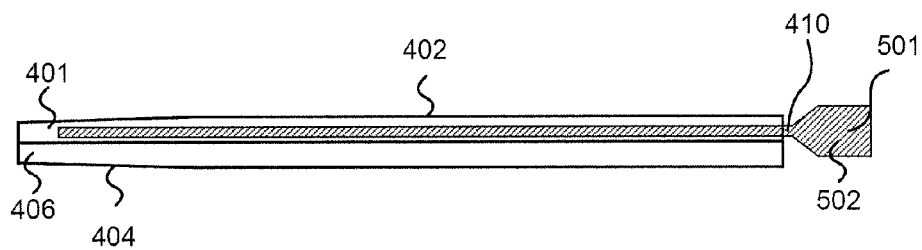
FIG. 5A is a side view illustrating one embodiment of a sphenocath apparatus with a stylus inserted into a lumen to straighten the sphenocath in accordance with the present invention.
Figure 5B:
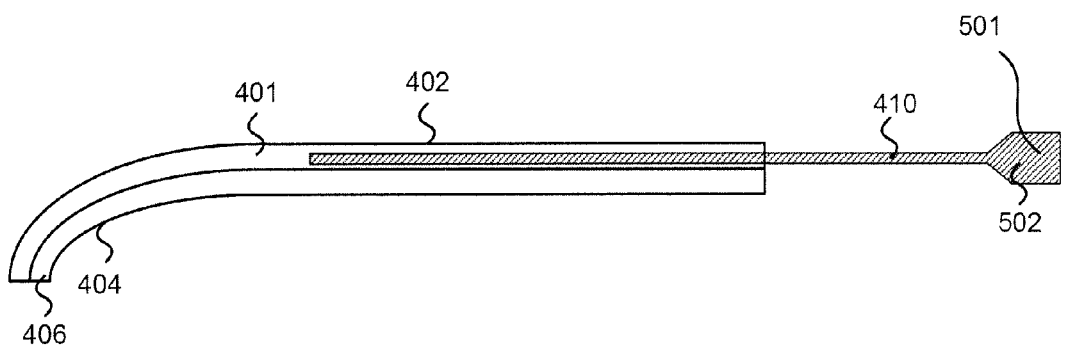
FIG. 5B is a side view illustrating one embodiment of a sphenocath with a stylus partially removed from the lumen such that the sphenocath curves according to an intrinsic curvature in accordance with the present invention.

FIG. 5A illustrates one embodiment of the catheter 402 portion of the sphenocath 400 with a rigid member 501 inserted into one of the lumens 401 or 403. The rigid member 501 in the embodiments illustrated in FIGS. 5A and 5B is a stylus 410 inserted into lumen 401 such that the sphenocath 400 is forced straight by the stylus 410. The stylus 410 comprises a rod, wire other rigid device having sufficient strength to straighten the intrinsic curve 404 of the catheter 402. With the sphenocath 410 straightened the catheter 402 can be inserted into the nasal cavity 104 until it reaches a point past the anterior ridge 302 of the middle sinus turbinate 114.

FIG. 5B illustrates an embodiment of the catheter 402 portion of the sphenocath 400 with the rigid member 501, in this case the stylus 410, partially removed from lumen 401. As the stylus 410 is removed from lumen 401, the catheter 402 bends due to the intrinsic curvature 404 of the catheter 402. Thus, once the sphenocath 400 has been inserted deep enough into the patient's nasal cavity 104 such that the tip has passed the middle sinus turbinate 114, the stylus 410 is withdrawn from lumen 401 to allow the catheter to bend at the intrinsic curvature 404. The sphenocath 400 may then be inserted all the way into the sphenopalatine/pterygopalatine recess 118 to deliver the anesthetic or medication to the sphenopalatine/pterygopalatine ganglia 120 or surrounding anatomical structure. In certain embodiments the radius of the intrinsic curvature 404 is sufficient to allow the catheter 402 to bend within the nasal cavity 104 to align the spray orifice 406 with the sphenopalatine/pterygopalatine recess 118. In one embodiment the intrinsic curvature 404 may bend between about 450 and about 90° to allow the catheter 402 to be placed within the sphenopalatine/pterygopalatine recess 118 without hitting the inferior surface 304 of the nasal bone 122 of the patient.

Figure 5C:
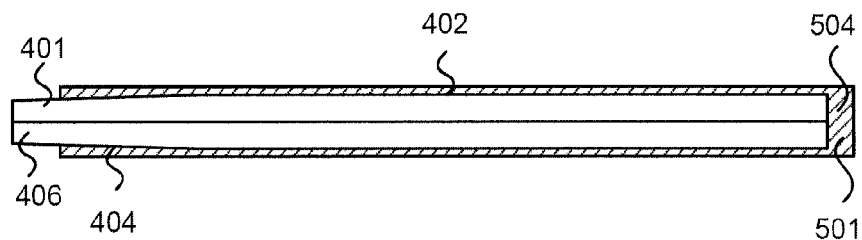
FIG. 5C is a side view illustrating one embodiment of a sphenocath apparatus with a catheter having an intrinsic curvature received within a sleeve to straighten the intrinsic curvature in accordance with the present invention.

FIG. 5C illustrates another embodiment of the catheter 402 portion of the sphenocath 400 with a rigid member 501 which surrounds the catheter 402. In this embodiment, the rigid member 501 is a sleeve 504 surrounding the catheter 402. In certain embodiments the sleeve 504 is sufficiently rigid to straighten the intrinsic curvature 404 when the catheter 402 is received within the sleeve 504. One of skill in the art will recognize that in certain embodiments, such as where a sleeve 504 is used in place of a stylus 410, the sphenocath 400 may include a single lumen catheter 402 rather than the multiple lumren catheter 402 illustrated in FIGS. 5A-5D. As discussed below with reference to FIGS. 6A-6C, in other embodiments, the catheter 402 may be configured with as many additional lumenas as may be required for additional complex procedures such as fiber optics for visually guiding the catheter into the sphenopalatine/pterygopalatine recess 118 or vacuum tubes configured to aspirate substances from within the sphenopalatine/pterygopalatine recess 118.

Figure 5D:
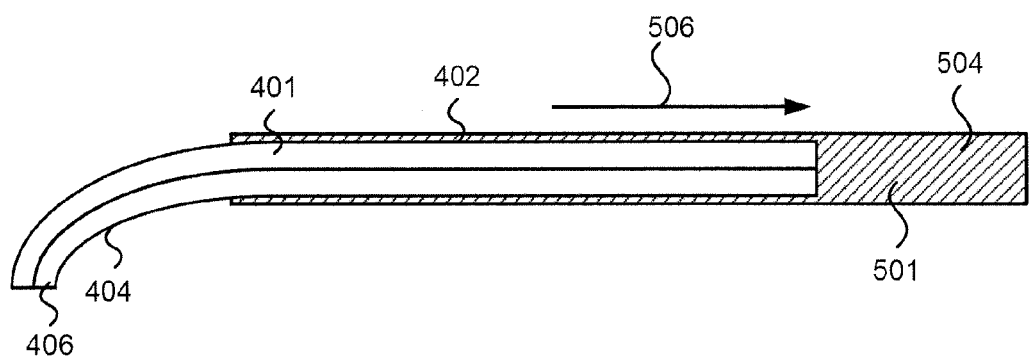
FIG. 5D is a side view illustrating one embodiment of a sphenocath with a catheter having an intrinsic curvature partially removed from a sleeve such that the intrinsic curvature curves in accordance with the present invention.

FIG. 5D illustrates an embodiment of the catheter 402 portion of the sphenocath 400 with the sleeve 504 partially withdrawn from the catheter 402 to expose the intrinsic curvature 404 of the catheter 402. As the sleeve 504 is removed from catheter 402 in the direction of arrow 506 the intrinsic curvature 404 of the catheter is no longer straightened by the sleeve 504. Therefore, the catheter 402 bends at the intrinsic curvature 404. Thus, once the sphenocath 400, including the sleeve 504, has been inserted deep enough into the patient's nasal cavity 104 such that the spray orifice 406 has passed the middle sinus turbinate 114, the sleeve 504 is withdrawn from catheter 402 to allow the catheter to bend at the intrinsic curvature 404. The sphenocath 400 may then be inserted all the way into the sphenopalatine/pterygopalatine recess 118 to deliver the anesthetic or medication to the sphenopalatine/ptervgopalatine ganglia 120 or surrounding anatomical structure.

Figure 6A:
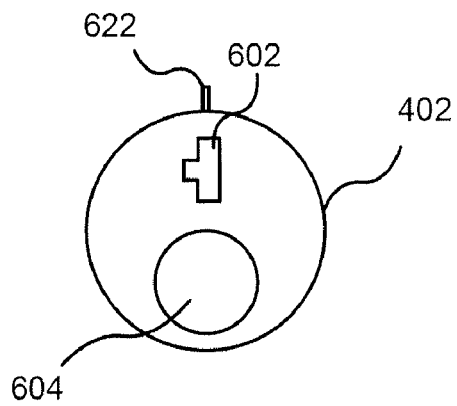
FIG. 6A is a cutaway view illustrating one embodiment of a catheter with a keyed lumen in accordance with the present invention.
Figure 6B:
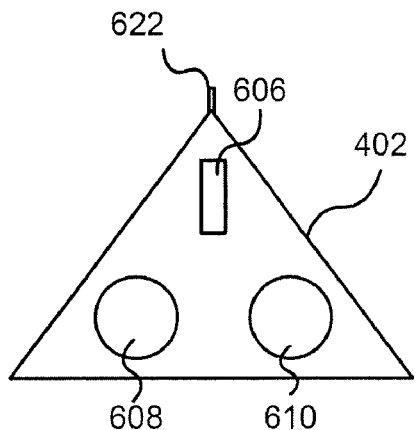
FIG. 6B is a cutaway view illustrating one embodiment of a catheter with three lumens in accordance with the present invention.
Figure 6C:
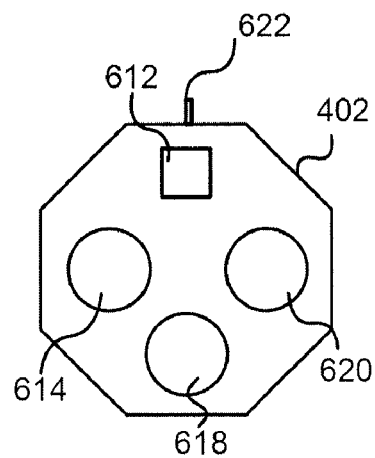
FIG. 6C is a cutaway view illustrating one embodiment of a catheter with four lumens in accordance with the present invention.

FIG. 6A through FIG. 6C illustrate various embodiments of a cross section of the catheter 402 of the sphenocath 400. In certain embodiments, such as the embodiment illustrated in FIG. 6A one of the lumens may be keyed to receive the stylus 410 in only one direction such as lumen 602. By keying lumen 602 to receive the stylus 410 in only one configuration, the pull tab of the stylus 410, such as pull tab 502 of FIGS. 5A and 513, may be configured to indicate the rotational direction of the spray orifice 406. Further, by keying one of the lumens to receive the stylus 410 in only one direction the entire sphenocath 400 may be rotated by the pull tab 502. Thus, in certain embodiments the rotational direction indicator 418 and a rotation tab 420 may be omitted where one of the lumens is keyed to receive the stylus 410 in only one direction. While the catheter 402 illustrated in FIG. 6a comprises a round structure with two lumens 602 and 604, one skilled in the art will recognize the catheter 402 structure may comprise any number of shapes such as the shapes illustrated in FIGS. 6B and 6C. One skilled in the art will recognize that the shape illustrated in FIG. 6A through FIG. 6C are for illustrative purposes only and are in no way limiting of the shapes which may comprise the catheter 402 and lumens 602, 604, 606, 608, 610, 612, 614, 616, 618 and 620.

In certain embodiments an additional orientation identifier 622 may be disposed on the top surface of the catheter 402. In one embodiment the orientation identifier 622 serves as an additional visual cue to assists the physician in determining the rotational orientation of the sphenocath 400 so that the physician will know which direction the intrinsic curvature 404 will bend when the stylus 410 is removed.

In the embodiments illustrated in FIG. 6A the catheter 402 comprises two lumens 602 and 604. In the embodiment illustrated in FIG. 6B the catheter 402 comprises three lumens 606, 608 and 610 and in the embodiment illustrated in FIG. 6C the catheter 402 comprises four lumens 612, 614, 618 and 620. One skilled in the art will recognize that the catheter 402 may be configured with as many additional lumens as may be required for additional complex procedures such as fiber optics for visually guiding the catheter into the sphenopalatine/pterygopalatine recess 118 or vacuum tubes configured to aspirate substances from within the sphenopalatine/pterygopalatine recess 118.

Figure 7:
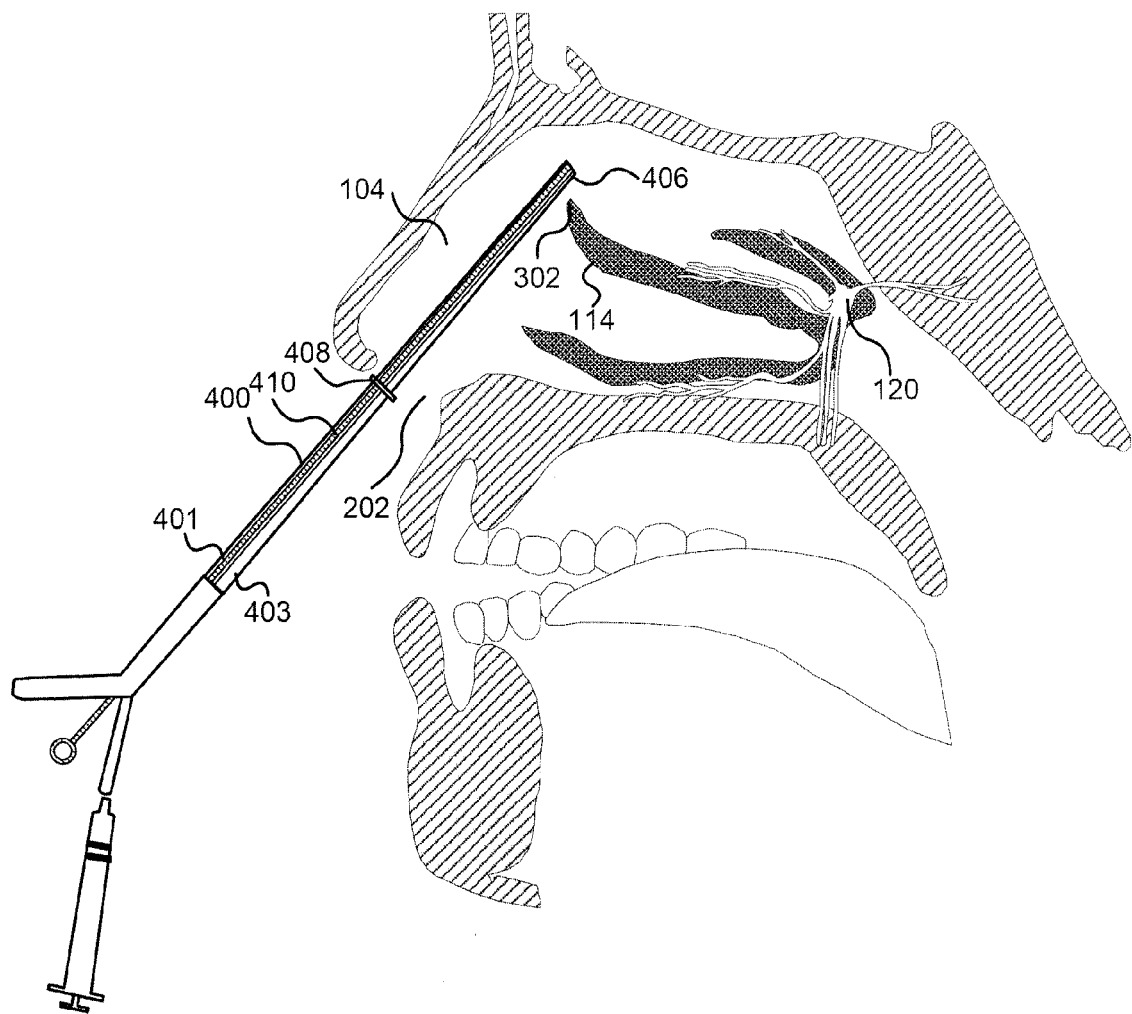
FIG. 7 is a cutaway view illustrating one embodiment of a sphenocath inserted within the nasal cavity of a patient in accordance with the present invention.

FIG. 7 illustrates one embodiment of the present invention wherein the sphenocath 400 is inserted through the nostril 202 into the nasal canal 104 and past the anterior ridge 302 of the middle sinus turbinate 114. To maintain a straight sphenocath 400 the stylus 410 is fully inserted into lumen 401 (note that either lumen 401 or 403 may be configured to receive the stylus 410). Depth indicator 408 is configured to signal the physician when the spray orifice 406 of the sphenocath 400 is sufficiently deep enough within the patient's nasal cavity 104 to clear the anterior ridge 302 of the middle sinus turbinate 114.

Figure 8:
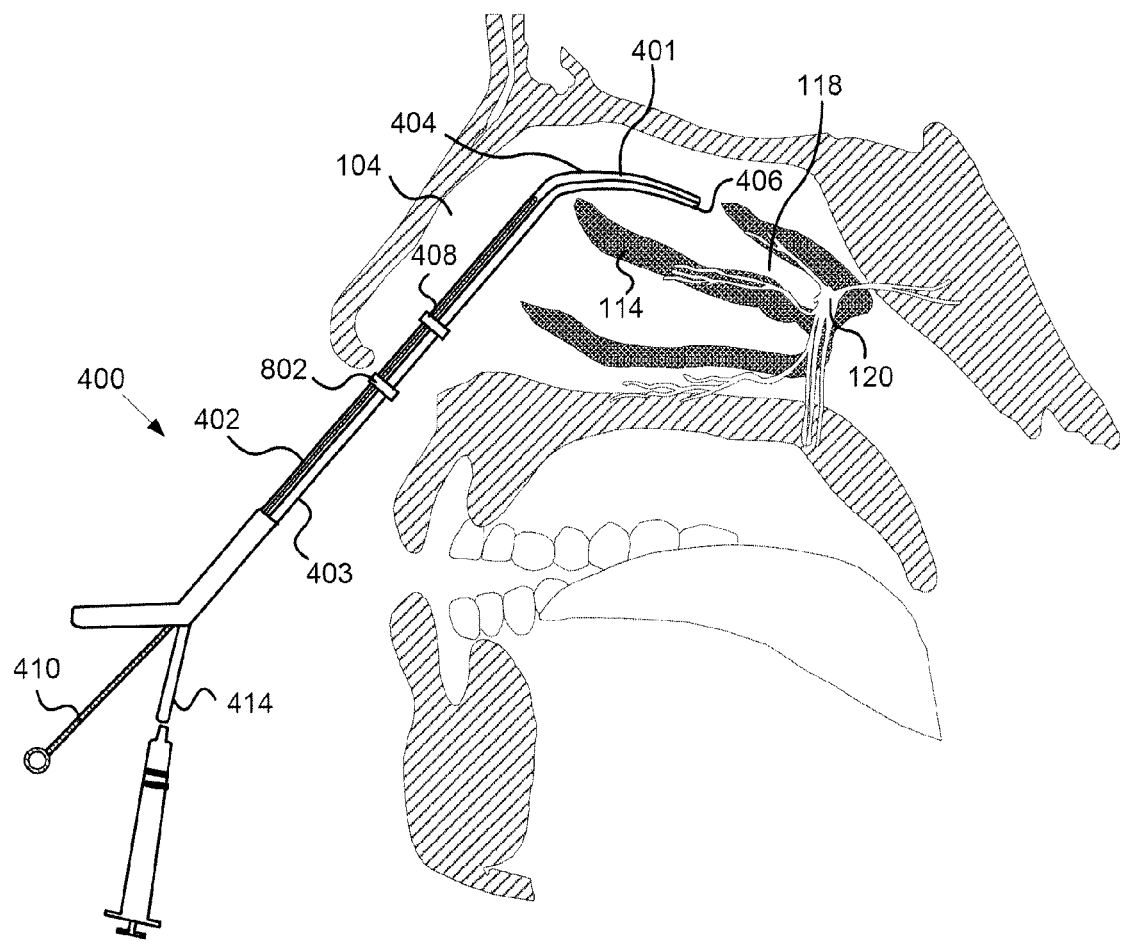
FIG. 8 is a cutaway view illustrating one embodiment of a sphenocath advanced into the sphenopalatine/pterygopalatine recess of a patient in accordance with the present invention.

FIG. 8 illustrates one embodiment of the present invention wherein spray orifice 406 of the sphenocath 400 has passed the middle sinus turbinate 114 and the stylus 410 has been partially withdrawn from within lumen 401. As the stylus is withdrawn from lumen 401 the catheter 402 bends due to intrinsic curvature 404 of the catheter 402. The sphenocath 400 can then be further inserted into the nasal cavity 104 deeper within the sphenopalatine/pterygopalatine recess 118. In certain embodiments a second depth indicator 802 may be disposed on the sphenocath 400 to identify the correct depth for administering the anesthetic or medication to the sphenopalatine/pterygopalatine ganglia 120 or surrounding anatomical structure. Once the sphenocath 400 is inserted to the correct depth the syringe 416 or other dispensing means delivers a desired amount of medication or anesthetic into the medication delivery port 414, through the lumen 403 to be dispersed at the spray orifice 406 to the sphenopalatine/pterygopalatine ganglia 120. Because the patient is in a supine position the medication or anesthetic pools in the sphenopalatine/ptervgopalatine recess 118.

The schematic flow chart diagram that follows is generally set forth as a logical flow chart diagram. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 9:
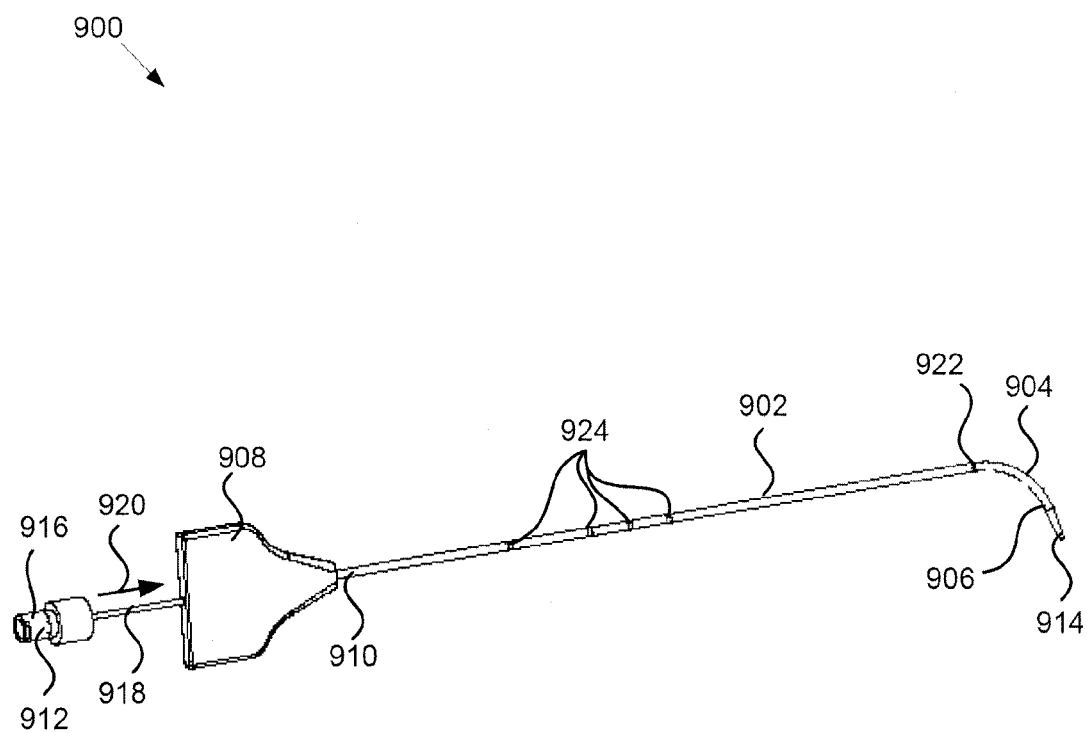
FIG. 9 is a side view illustrating one embodiment of a sphenocath apparatus for treating headaches in accordance with the present invention.

FIG. 9 illustrates another embodiment of a sphenocath 900 having a catheter 902 portion which includes an intrinsic curvature 904 near an insertion end 906 and a rotation tab 908 near a manipulation end 910. In certain embodiments the sphenocath 900 also includes a medication delivery port 912 located near the manipulation end 910 and a spray orifice 914 located at the insertion end 906.

In the embodiment illustrated in FIG. 9, the medication delivery port 912 includes a Luer fitting 916 keyed to fit a syringe (not shown). The medication delivery port 912 is fluidly connected to the catheter 902 portion through a stylet tube 918. In certain embodiments the stylet tube 918 is sufficiently rigid to straighten the intrinsic curvature 904 in the insertion end 906 of the catheter 902 when the stylet tube 918 is inserted into the catheter 902 in the direction of arrow 920. As the stylet tube 918 is withdrawn from the catheter 902 in a direction opposite arrow 920, past a point where the stylet tube 918 support the intrinsic curvature 904, the catheter 902 bends due to the intrinsic curvature 904. For example, once the stylet tube 918 is withdrawn from the catheter 902 past a certain point (such as point 922) the catheter 902 bends in the direction shown due to the intrinsic curvature 904. In certain embodiments the catheter 902 may begin to bend immediately as the stylet tube 918 is withdrawn from the catheter 902. In other embodiments catheter 902 only bends once the stylet tube 918 has been removed past a point 922 where the intrinsic curvature 904 begins.

In certain embodiments the manipulation end 910 of the spenocath 900 includes a rotation tab 908 for directing the spray orifice 914 in the direction of the sphenopalatine/pterygopalatine recess 118 when the spray orifice 914 has passed the middle sinus turbinate 114. The rotation tab 908 may be aligned with the intrinsic curvature 904 in a predefined orientation to signal to the physician the direction of the spray orifice 916 when the sphenocath 900 is disposed within a patient's nasal cavity 104. As discussed above, the sphenocath 900 may include depth indicators 924 to signal a proper depth within the nasal cavity 104 to insert the sphenocath 900 into sphenopalatine/pterygopalatine recess 118.

Figure 10:
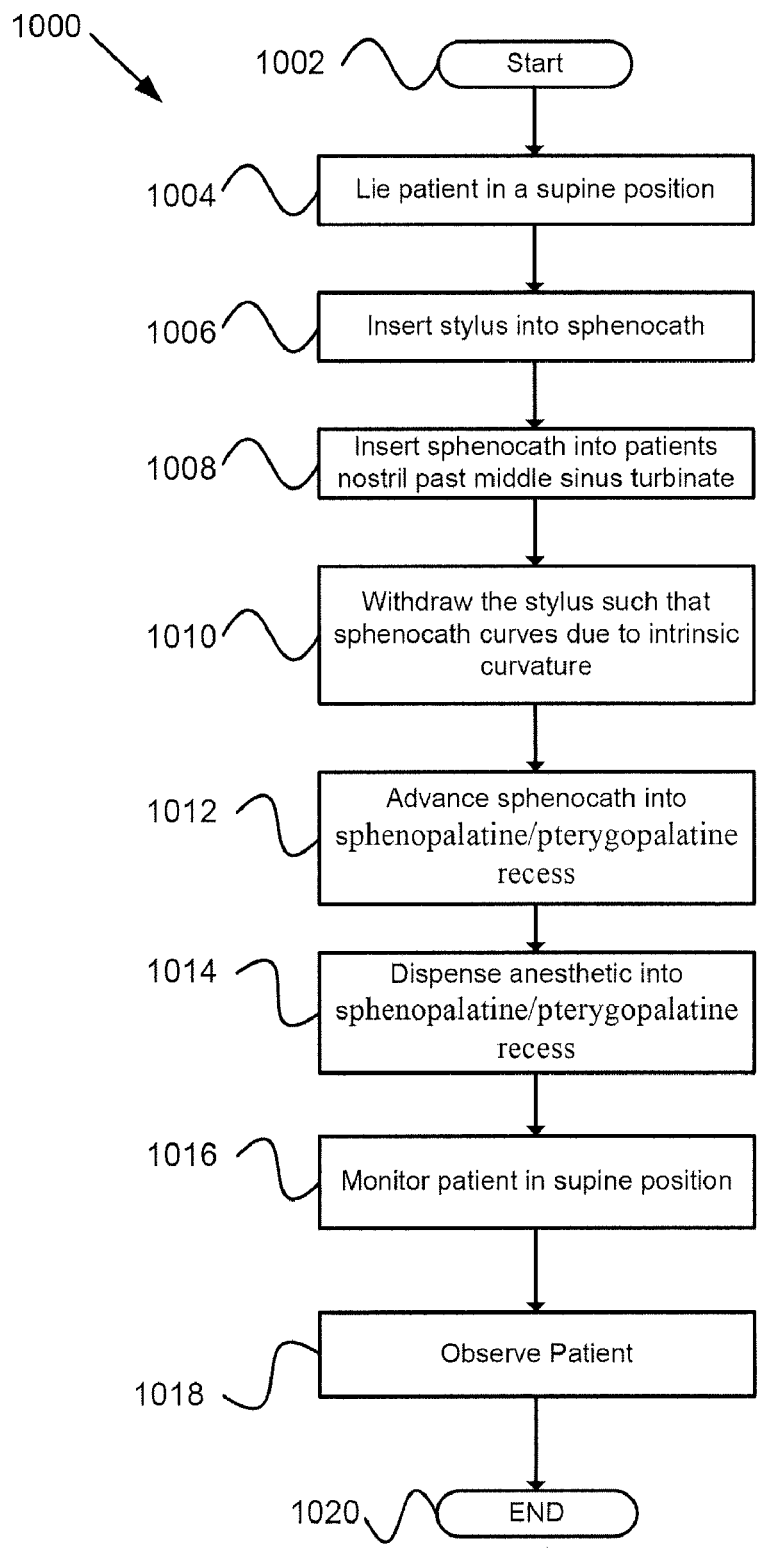
FIG. 10 is a schematic block diagram illustrating one embodiment of a method for treating headaches in accordance with the present invention.

FIG. 10 is a schematic flow chart diagram illustrating one embodiment of a method 1000 for treating sympathetic mediated cephalgia (headaches.) In one embodiment the method starts 1002 and the patient is placed in a supine position. In certain embodiments, the patient may already be in the supine position. In other embodiments, the physician may wish to administer the treatment with the patient in a standing or seated position and thus, this step may be omitted.

The physician inserts 1006 a stylus, such as stylus 410 into a lumen within a sphenocath such as the sphenocath 400 of FIG. 4. The stylus 410 may act to straighten the sphenocath 400 to allow for easy insertion into a patients nasal cavity 104. In certain embodiments the stylus 410 may already be inserted within the lumen and thus this step may be omitted.

The sphenocath 400 is inserted 1008 into the patient's nostril 202 and advanced through the nasal cavity 104 to a position wherein the spray orifice 406 of the sphenocath 400 has passed the middle sinus turbinate 114. The stylus 410 is withdrawn 1010 from the sphenocath 400 such that the sphenocath 400 curves due to an intrinsic curvature 404 of the catheter 402. The sphenocath 400 is advanced 1012 into the sphenopalatine/pterygopalatine recess 118. Anesthetic is dispensed 1014 into the sphenopalatine/pterygopalatine recess 118.

The anesthetic may cause a temporary loss of sensation in the nasal cavity and may, in certain instances, drain into the patients throat causing a loss of sensation in the patients throat. Therefore, in certain embodiments the physician may monitor 1016 the patient in the supine position for a period of time to make sure that the patient does not have any adverse reactions to the anesthetics. In one embodiment the patient may be observed 1018 to determine the efficacy of the procedure and the method ends 1020.

The present invention may be embodied in other specific forms without departing from its spirit or essential characteristics. The described embodiments are to be considered in all respects only as illustrative and not restrictive. The scope of the invention is, therefore, indicated by the appended claims rather than by the bforegoing description. All changes which come within the meaning and range of equivalency of the claims are to be embraced within their scope.

The invention claimed is:

1. A method for treating migraines, the method comprising, in combination:
 inserting a catheter having a straightening member into the nostril of a patient,
  the catheter further comprising an insertion end and a manipulation end,
  the insertion end having an intrinsic curvature with respect to the longitudinal axis of the catheter and the straightening member is disposed within the catheter,
  the intrinsic curvature conforming to a patient's nasal anatomy such that the catheter is insertable into the sphenopalatine recess of the patient;
 advancing the catheter with the straightening member inserted into the catheter past the middle sinus turbinate within the nasal cavity of the patient;

removing the straightening member from the catheter whereby the catheter bends in a direction toward the patient's sphenopalatine recess;

advancing the catheter into the patient's sphenopalatine recess; and, dispensing medication to the patient's sphenopalatine ganglion disposed within the sphenopalatine recess of the patient.

2. The method of claim 1, further comprising identifying a direction of the intrinsic curvature and aligning the intrinsic curvature of the catheter with the patient's sphenopalatine recess.

3. The method of claim 1, further comprising identifying a defined depth of the catheter, the defined depth comprising a depth equaling a distance between an entrance to a patient's sphenopalatine recess and an external entrance to the patient's nostril.

4. The method of claim 3, wherein medication is delivered over the middle sinus turbinate to achieve sphenopalatine ganglion blockade.

5. The method of claim 4, whereby the spatial configuration of the catheter enables ingress without insult or injury to nasal tissue.

6. The method of claim 4, whereby the spatial configuration of the catheter enables egress without insult or injury to nasal tissue.

7. The method of claim 4, wherein the sympathetic nerves of the patient are impacted by accessing the sphenopalatine recess at the back of the sinus cavity extending from the top of the middle sinus turbinate.

8. The method of claim 7, wherein the sphenopalatine ganglion blockade is not achieved by saturation of different areas within the sinus cavity or the throat of the patient.

9. The method of claim 3, wherein transnasal sphenopalatine ganglion blockade is achieved by delivery of medicine over the middle sinus turbinate.

10. The method of claim 3, wherein the depth measurements enable access without insult or injury to internal nasal tissues.

* * * * *

UNITED STATES PATENT AND TRADEMARK OFFICE
CERTIFICATE OF CORRECTION

| | | |
|---|---|---|
| PATENT NO. | : 8,388,600 B1 | Page 1 of 1 |
| APPLICATION NO. | : 13/629997 | |
| DATED | : March 5, 2013 | |
| INVENTOR(S) | : Stephen Eldredge | |

It is certified that error appears in the above-identified patent and that said Letters Patent is hereby corrected as shown below:

On the title page:

Immediately under "(22) Filed: Sep. 28, 2012" add:

--Related U.S. Application Data
(60) Provisional application No. 61/094,323 filed on Sep. 4, 2008,
(62) Divisional of U.S. patent application Ser. No. 12/553,953 filed on Sep. 3, 2009.--

In the claims:

Col. 13, In Claim 3, line 15, "entrance to a" should be --entrance to the--

Col. 13, In Claim 3, line 16, "an external" should be --the external--

Signed and Sealed this
Twenty-ninth Day of October, 2013

Teresa Stanek Rea
*Deputy Director of the United States Patent and Trademark Office*